United States Patent
Elson et al.

[19]

[11] Patent Number: 6,015,397
[45] Date of Patent: Jan. 18, 2000

[54] NEEDLE POINT GUARD SAFETY CAP ASSEMBLY

[76] Inventors: Edward E. Elson, 4356 Claytor Cir., Anaheim, Calif. 92806; Lawrence R. Koh, 11755 Wilshire Blvd., 9th Flr., Los Angeles, Calif. 90025

[21] Appl. No.: 09/160,511

[22] Filed: Sep. 24, 1998

Related U.S. Application Data

[63] Continuation-in-part of application No. 08/879,879, Jun. 20, 1997, Pat. No. 5,814,018.

[51] Int. Cl.[7] ...................................................... A61M 5/00
[52] U.S. Cl. .......................... 604/192; 604/198; 604/263
[58] Field of Search .................................. 604/110, 192, 604/187, 198, 263

[56] References Cited

U.S. PATENT DOCUMENTS

| | | | |
|---|---|---|---|
| 4,735,618 | 4/1988 | Hagen | 604/110 X |
| 5,538,508 | 7/1996 | Steyn | 604/192 |
| 5,700,249 | 12/1997 | Jenkins | 604/263 |
| 5,738,665 | 4/1998 | Caizza et al. | 604/263 |
| 5,823,997 | 10/1998 | Thorne | 604/192 X |

*Primary Examiner*—John D. Yasko
*Attorney, Agent, or Firm*—Gene W. Arant; Larry D. Baker

[57] ABSTRACT

A needle point cover assembly for securely covering and protecting the needle point after a syringe has been used includes a cover in the form of an elongated hollow member that is open at one end for receiving the needle therein, and at its other end is mostly enclosed by an end wall having a hole through which the needle can pass. A lid encloses the otherwise open end of the cover member. The lid has a hole through which the needle may pass so that the needle may extend through both the lid hole and the hole in the end wall. When the syringe is being used to make an injection, the needle point projects through the hole in the end wall. After an injection has been made and the syringe is ready for disposal, a manually actuable extensible frame slides the cover to where its end wall is beyond the extremity of the needle point. The cover member can then be supported by the hole in the lid and rotated about the lid hole until the needle point passes inside the enclosed end wall of the cover member into a protected position where it cannot pass through the cover member hole.

22 Claims, 5 Drawing Sheets

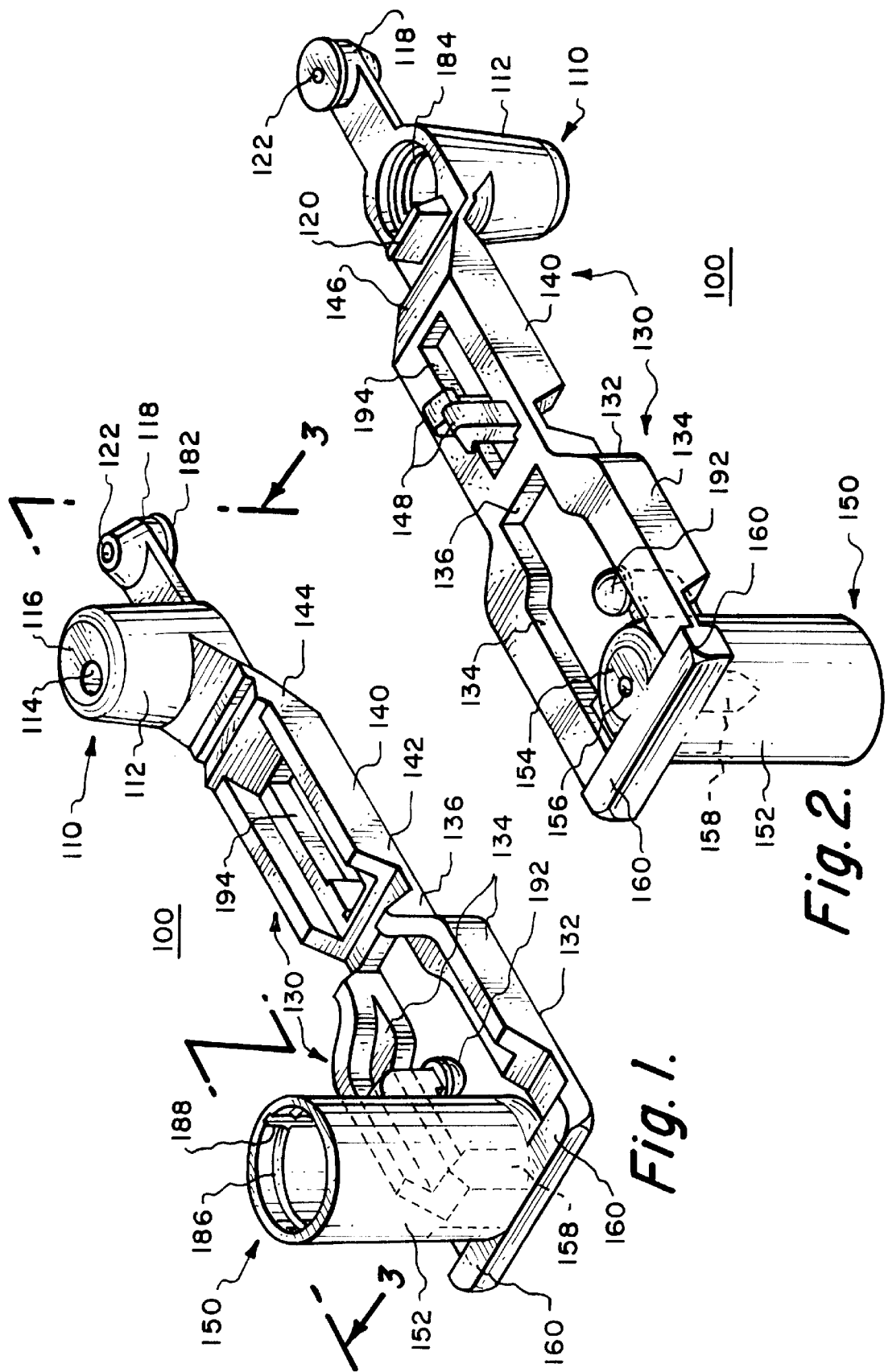

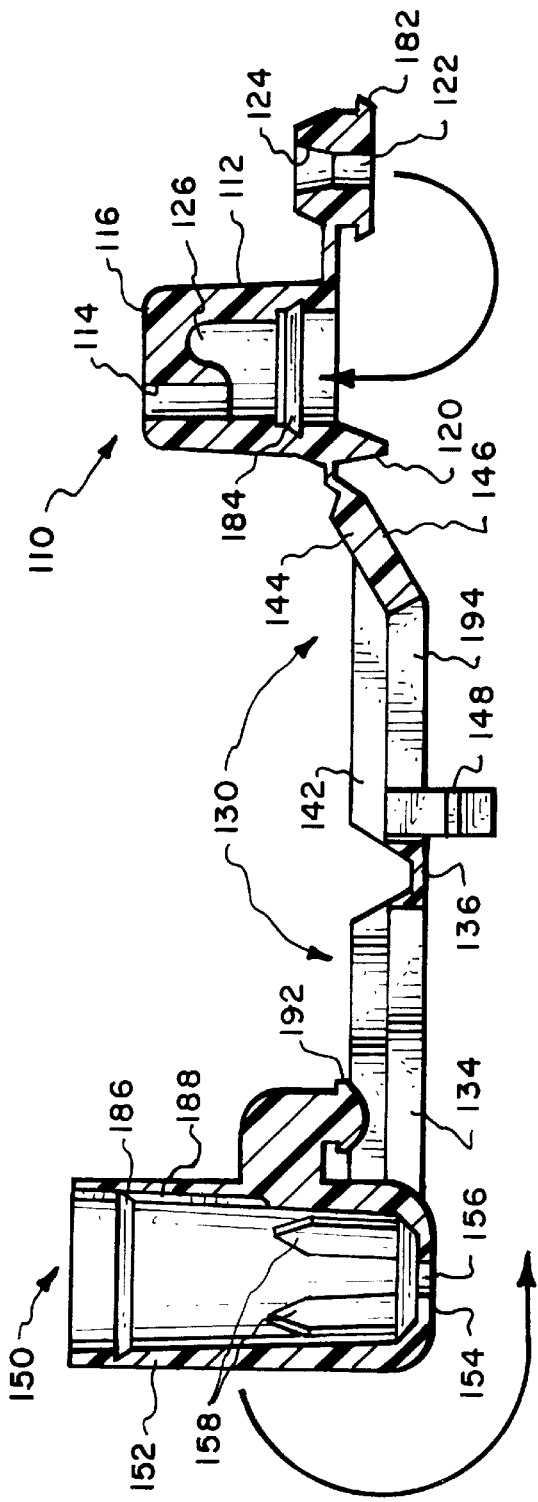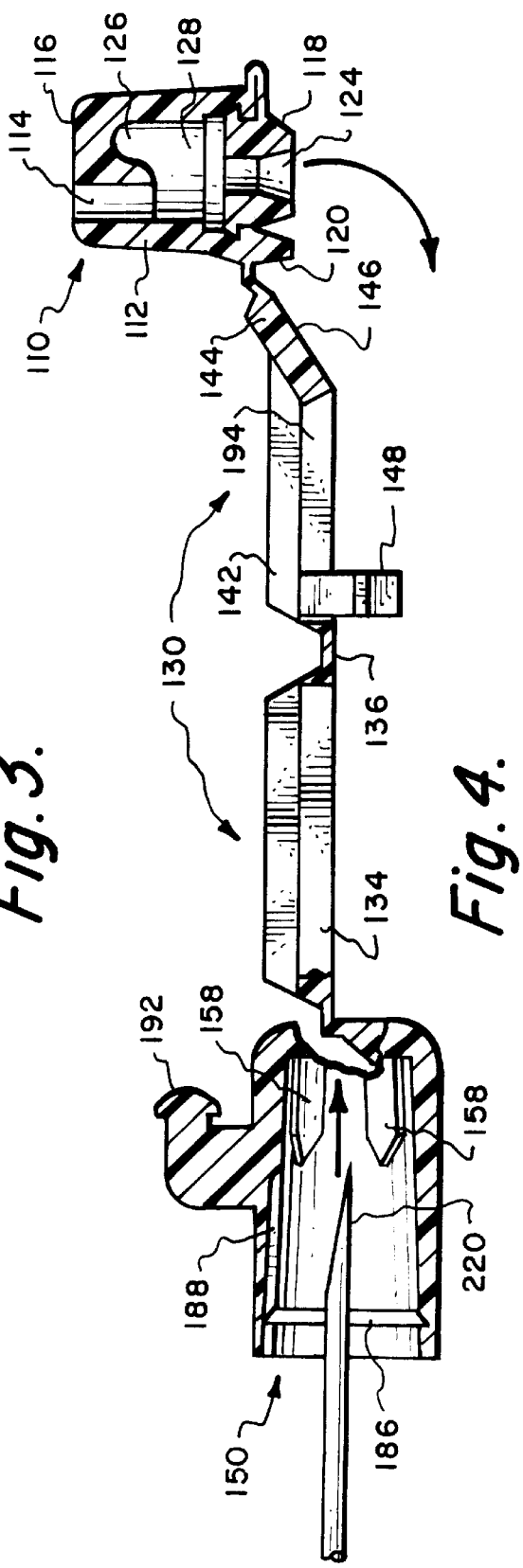

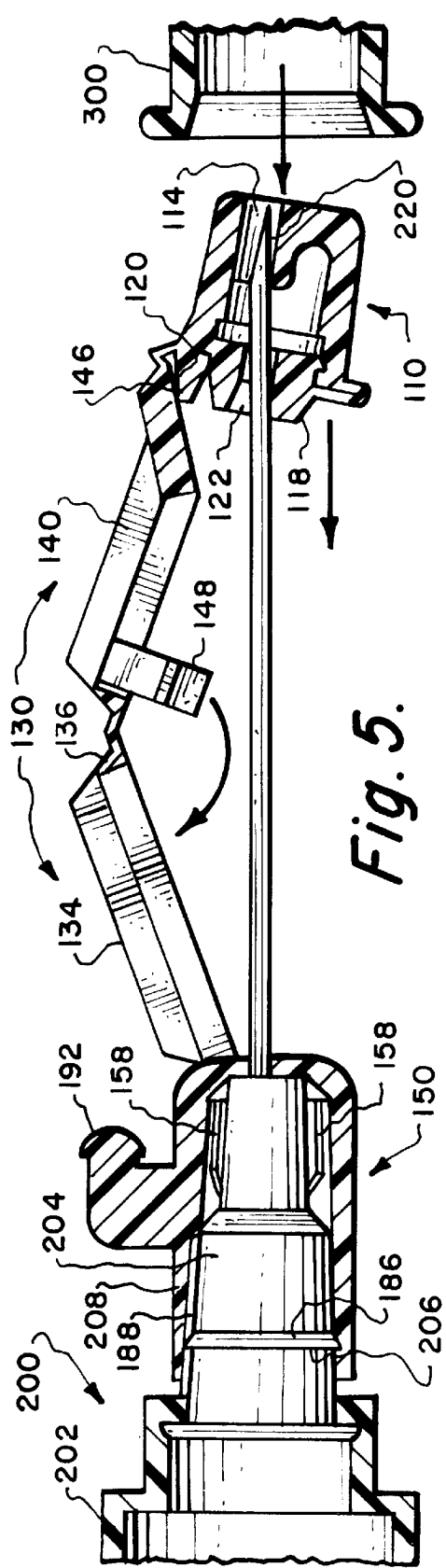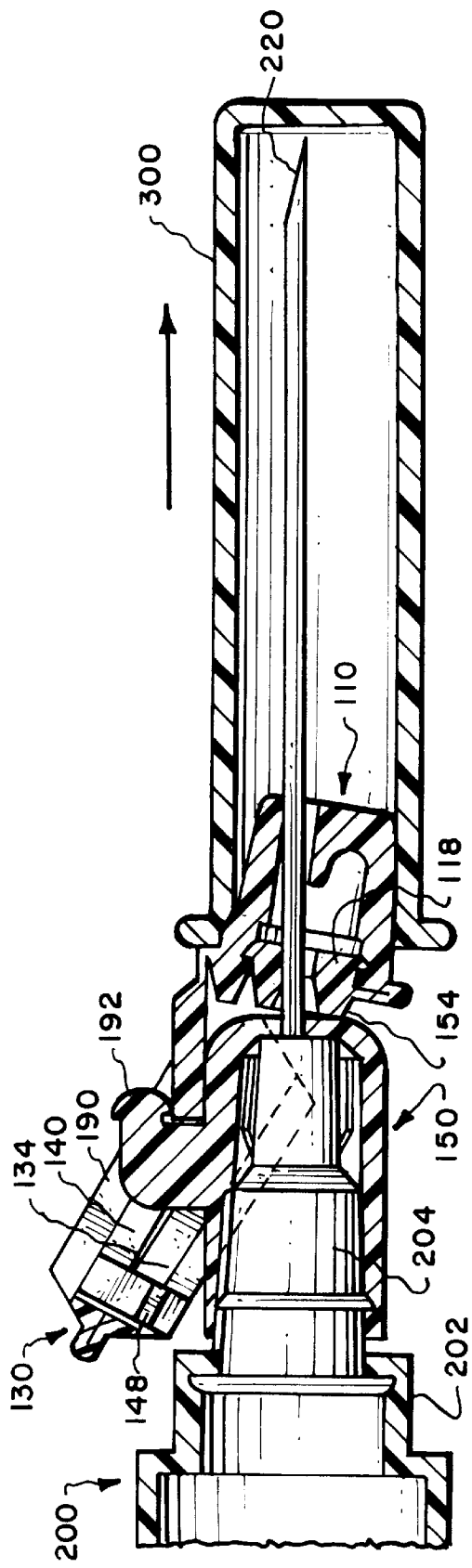

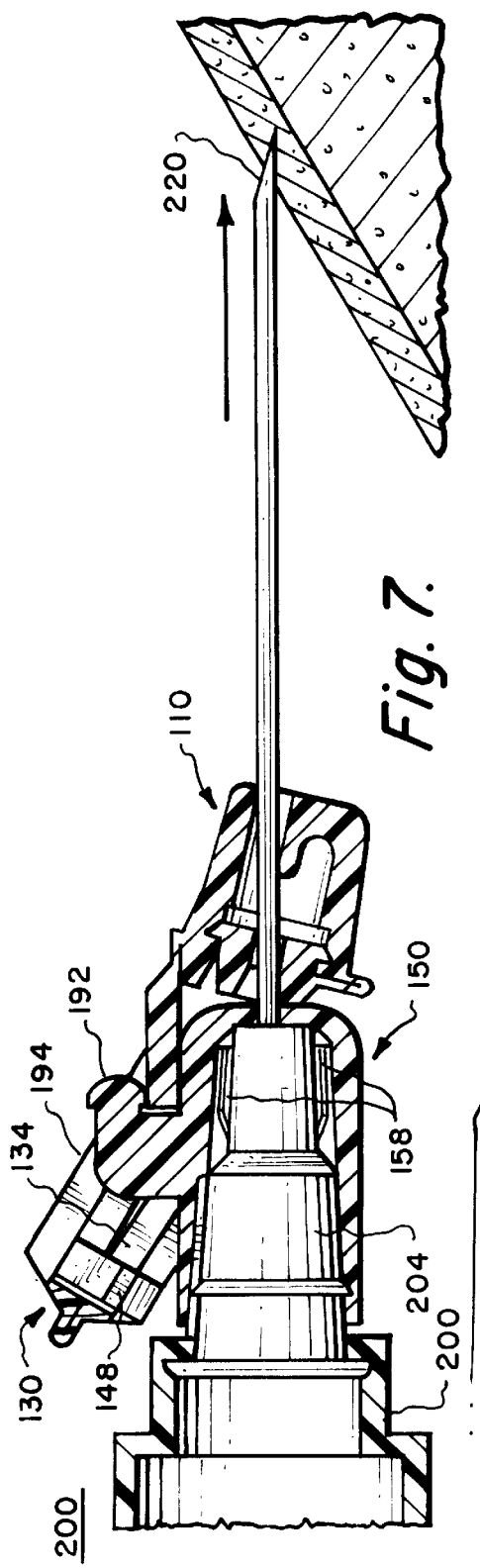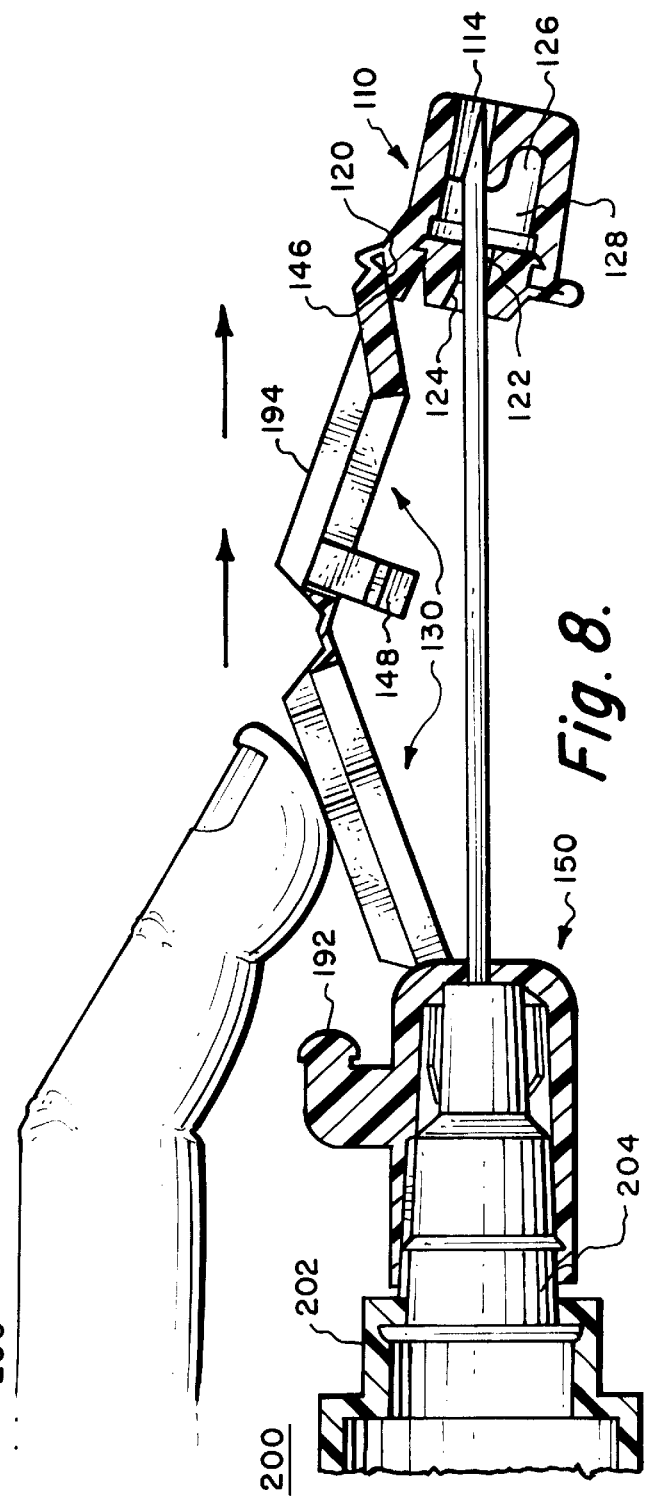

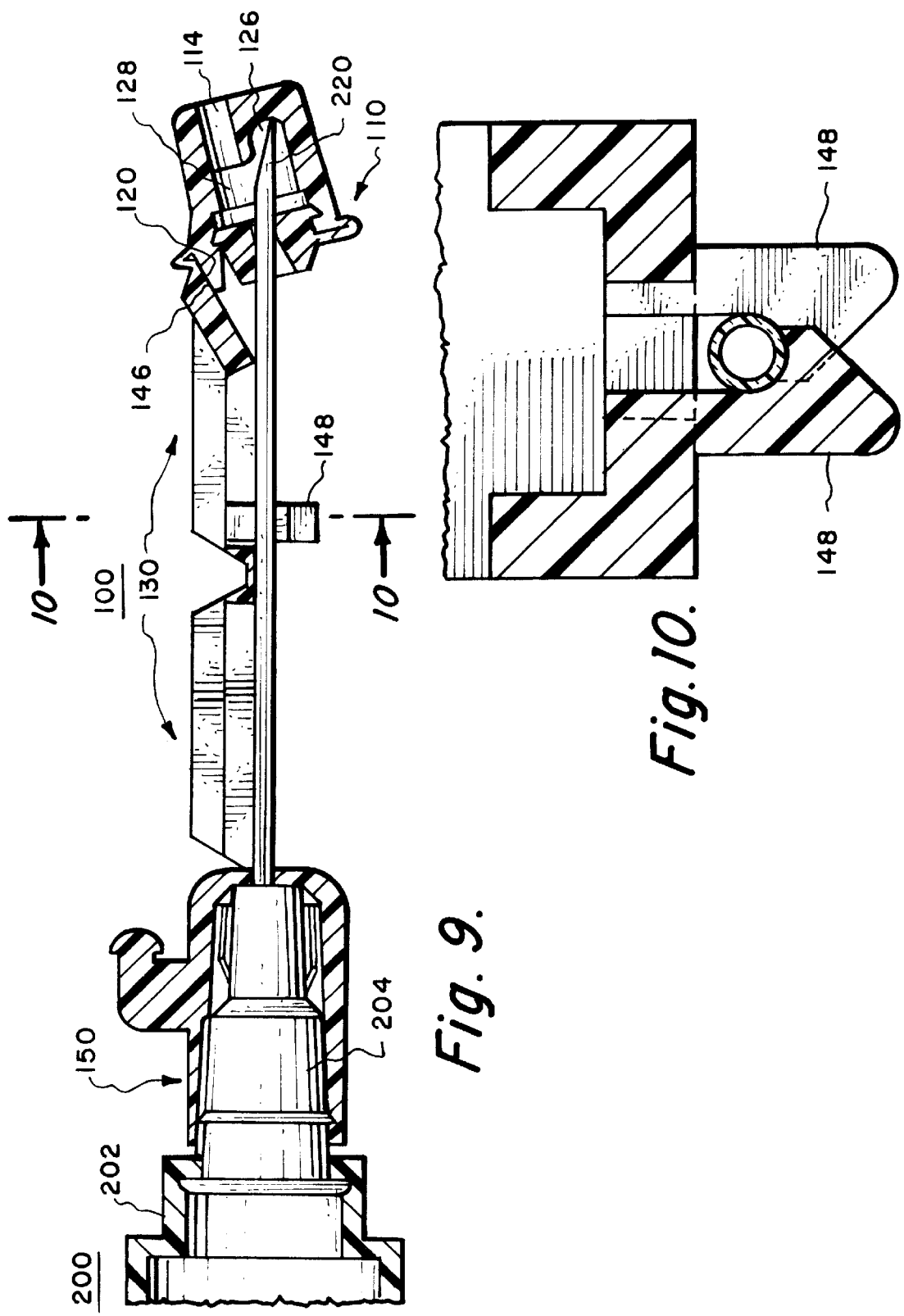

NEEDLE POINT GUARD SAFETY CAP ASSEMBLY

RELATED APPLICATION

This application is a continuation-in-part of our U.S. application Ser. No. 08/879879 which was filed on Jun. 20, 1997 now U.S. Pat. No. 5,814,018.

FIELD OF THE INVENTION

The present invention relates to the field of hypodermic needles. More specifically the present invention relates to the Covering of a hypodermic needle point after use to prevent accidental sticks when disposing of the hypodermic needle.

BACKGROUND OF THE INVENTION

Today, disposable hypodermic needles are an integral part of health care. Typical hypodermic needles include a replaceable plastic sheath which must be removed prior to use and subsequently replaced prior to disposal. The act of replacing the needle cap exposes the user, typically hospital or medical personnel, to accidental needle sticks. An accidental needle stick can transmit diseases through the body's first line of defense—the skin. Because some diseases such as HIV are presently incurable and can ultimately lead to death, the exposed point of a used needle and every needle sheath replacement is potentially life threatening. Although prior devices have addressed this problem, until now an effective and economical device has not been found.

SUMMARY OF THE INVENTION

According to the present invention a needle point cover assembly is provided that securely covers and protects the needle point after a syringe has been used. The assembly preferably includes a cover in the form of an elongated hollow member that is open at one end for receiving the needle therein, and at its other end is mostly enclosed by an end wall having a hole through which the needle can pass. A lid typically encloses the otherwise open end of the cover member. The lid has a hole through which the needle may pass so that the needle may extend through both the lid hole and the hole in the lid wall.

When the syringe is being used to make an injection, the needle point must project through the hole in the end wall. An extensible frame that is manually actuable can be attached to the cover member for moving the cover member along the needle when the syringe is being readied for disposal.

After an injection has been made and the syringe is ready for disposal, the cover is then slid to where its end wall is beyond the extremity of the needle point. The cover member can then be supported by the hole in the lid and rotated about the lid hole until the needle point passes inside the enclosed end wall of the cover member into a protected position where it cannot pass through the cover member hole.

The needle point cover assembly incorporates several elements to provide tactile and aural feedback to the user to indicate that the needle cover has been successfully deployed. Upon initially coaxing the extensible frame from its non-actuated position, a latch arm member which serves to retain the frame prior to use "snaps" through a slot in the frame; upon full deployment of frame, tabs on the frame "snap" around the needle shaft. The tactile and aural feedback serves to provide reassurance to the user that the needle has been rendered safe without requiring visual inspection of the needle.

The latch arm and slot, in addition to providing the user with tactile feedback, insure that once deployment of the needle shield has been initiated, sufficient momentum is present in the finger of the user to complete deployment. To overcome the resistance of the lever arm as it is pulled through the slot, the user must provide enough force against the extensible frame that, once the lever arm clears the slot, deployment is completed in a single motion, without any additional attention by the user.

Since the user applies force to the needle shield in a direction which could cause the needle shield to be pushed off the hypodermic entirely if it were not adequately retained in some manner, the preferred embodiment of the needle shield incorporates an annular slot which engages a corresponding annular ring on the hypodermic. In some situations it is also important that cannula opening at the tip of the hypodermic be properly oriented. The preferred embodiment may also incorporate a longitudinal slot to engage a corresponding rib on the hypodermic. In such situations, the needle shield provides an added indication of the cannula orientation.

The preferred embodiment is integrally formed of a resilient plastic, making it economical to manufacture.

BRIEF DESCRIPTION OF THE DRAWINGS

FIG. 1 is a perspective view of one side of the presently preferred embodiment of the needle point guard safety cap assembly.

FIG. 2 is a perspective view of the flip-side of the embodiment shown in FIG. 1.

FIG. 3 is a cross-section at 3—3 of FIG. 1.

FIG. 4 is a cross-section at 3—3 of FIG. 1 when the needle point guard safety cap assembly is prepared for attachment to a syringe.

FIG. 5 is a cross-section of the presently preferred embodiment of FIG. 1 illustrating the needle point guard safety cap assembly attached to a syringe.

FIG. 6 is a cross-section of the presently preferred embodiment of FIG. 1 illustrating the needle point guard safety cap assembly attached to a syringe with a needle sheath covering the needle.

FIG. 7 is a cross-section of the presently preferred embodiment of FIG. 1 illustrating the needle point guard safety cap assembly attached to a syringe with the needle sheath removed so that the syringe is ready for use.

FIG. 8 is a cross-section of the presently preferred embodiment of FIG. 1 illustrating the needle point guard safety cap assembly attached to a syringe showing how the user actuates the assembly to cover the needle point.

FIG. 9 is a cross-section of the presently preferred embodiment of FIG. 1 illustrating the needle point guard safety cap assembly attached to a syringe and depicting the rotated needle point cap covering the needle point and secured in a protected position after use.

FIG. 10 is a cross-section at 10—10 of FIG. 9 illustrating the clips which secure the needle guard safety cap to the needle when the guard is deployed.

DETAILED DESCRIPTION

With the needle point guard safety cap assembly of present invention, accidental needle sticks occurring after needle use can be virtually eliminated. To prevent accidental needle sticks, the present invention utilizes a cover or cap or cup-shaped member to cover or contain the point of the needle in a protected position after use.

The needle point cover has a hole so that it can be slid along the needle to a stowed position distal from the point prior to injection and then slid back along the needle to cover the point after injection. Once the point of the needle is within the cover after injection, the cover is rotated or skewed so that the needle point can not re-emerge through the hole in the cover. A well chamber formed in the end of the cover serves to capture the end of the needle an prevent it from re-emerging through the hole in the end wall.

The needle point cover is typically adapted to receive a typical needle sheath. As such, the needle point guard safety cap assembly typically can be installed prior to sheath installation and needle distribution. Needles can therefore be distributed with the needle point cover stowed distal the point and with the sheath covering the needle in the normal fashion.

In preparation for injection, the needle sheath is removed and the syringe is then used in the normal fashion to administer the injection. After injection, the needle point cover can be slid the length of the needle and rotated to prevent re-emergence of the needle point.

To facilitate rotation of the needle point cover and to provide a convenient means for sliding the cover along the needle, as well as to facilitate connection to a needle hub or syringe, the needle point guard safety cap assembly may also have a collapsible extension or extendible frame coupled to the needle point cover. The extension or frame can in turn be coupled to an attachment member which is adapted to attach to the needle hub in a non-releasable fashion. The needle hub in turn may be pre-assembled to a syringe or a syringe may be attached to the needle hub prior to use in injecting or withdrawing fluids from a patient.

To help retain the needle point cover on the needle hub, the preferred embodiment incorporates an annular groove which mates with a annular ring on the needle hub.

During sheath removal prior to injection, typically, the frame in co-operation with the attachment member, retains the needle point cover in its stowed position distal the needle point. In the preferred embodiment, a protrusion on the attachment member engages a slot on the frame; the enlarged end of the protrusion "snaps" through the slot when the needle shield is actuated. After injection, the frame can be manually actuated or urged so that the needle point cover is released to slide toward and eventually cover the point.

After the point is contained within the cover, rotation can be made to occur in response to urging of the frame. Once the point of the needle is within the cover, further urging of the frame causes the cover to rotate. The rotated cover prevents the needle point from re-emerging through the hole in the cover by retaining the needle point in a well chamber formed in the cover end wall.

As a further assistance to maintaining the rotational position of the cover, the frame typically can be locked or secured to the needle shaft. Securing the frame also prevents the frame from collapsing and allowing the cover to slide back up the needle shaft which further ensures that the needle point can not be re-exposed.

Installation of the presently Preferred Embodiment

The needle point guard safety cap assembly 100 of the present invention can be manufactured of a unitary molded plastic piece to increase reliability and to reduce manufacturing and installation cost. Although not required, the presently preferred embodiment of the present invention is of a unitary molded plastic piece.

The present invention is designed to be installed prior to needle use. It typically would be installed on the needle or syringe prior to distribution. The steps necessary to install the presently preferred embodiment are shown by the arrows in FIGS. 1–5.

To install the presently preferred embodiment of the needle point guard safety cap assembly, the syringe attachment member and the needle point cover must be rotated into position to receive the needle. The syringe attachment member and frame are flexibly coupled. The syringe attachment member or base cup 150 is therefore rotated approximately 90 degrees with respect to the frame 130 so that the needle can extend through the syringe attachment member 150 approximately parallel to the extended frame 130.

Next, a lid or enclosing member 118, which is flexibly coupled to the needle point cover 110, is rotated to plug or enclose the cover 110. To help retain the lid to the cover, an annular ring 182 on the lid engages an annular slot 184 on the cover member; the ring and slot may have tapered cross sections to allow them to engage easily, but which make them difficult to separate.

The enclosed cover 110, which is flexibly coupled to the frame 130, is then rotated so that the needle can pass through both the hole in it and a hole in the syringe attachment member 150.

As the cover is positioned to receive the needle, the frame or segmented extension 130 begins to collapse or fold at a flexible portion between the segments. The cover 110 is then slid along the needle shaft away from the needle point. To assist with this, as well as to position the cup-shaped member prior to needle insertion, a needle sheath 300 can be placed over the cover 110 in order to more easily manipulate the cover 110.

As the cover 110 is slid along the shaft, the frame or collapsible extension 130 continues to fold. As the cover closely approaches or contacts the needle hub or syringe, the frame 130 in co-operation with the syringe attachment member 150, releasably retains the cover. In the preferred embodiment, a protrusion 192 with an enlarged head on the syringe attachment member passes through a slot 194 on the frame. The enlarged head of the protrusion is sized such that when appropriate force is applied to the frame the head "snaps" through the slot.

By using the sheath 300 to slide the cover 110 down the needle shaft, it too is installed in preparation for distribution. To retain the needle shield to the needle hub, the preferred embodiment incorporates an annular slot 186 on the inside of the attachment member which engages a corresponding annular ring 206 on the needle hub. The ring and slot may have tapered cross sections to allow them to engage easily, but which make them difficult to separate. Sheath 300 removal prior to an injection does not disturb the retained cover 110, however, the frame can be released by the user to actuate the cover.

The presently Preferred Embodiment FIGS. 1–10

FIGS. 1–10 illustrate one embodiment of the needle point guard safety cap assembly 100 of the present invention. It is presently preferred to form the needle point guard safety cap assembly of a unitary plastic piece. As such, FIGS. 1 & 2 depict alternate sides of the presently preferred needle point guard safety cap assembly as it appears after it is removed from a mold. FIGS. 3–10 depict the presently preferred embodiment as it is being prepared for use and in actual use with a syringe.

Turning to FIGS. 1 & 2, the needle point guard assembly or needle point cover 100 comprises the needle point cap or cup-shaped member or needle point covering means 110 for covering the point of the needle. The needle point cap or cover 110 is shaped in the form of an elongated member having a circumferential wall 112. One end of the elongated member 112 is open while the other is mostly enclosed by a bottom or end wall 116.

In the presently preferred embodiment of FIGS. 1 & 2, the hole or bore 114 in the bottom wall 116 of the needle point cap 110 allows the needle to pass through. The hole 114 is off-centered in the bottom wall, with the a well chamber 126 occupying most of the remaining wall area. A lever arm or rotating means 120 attached to the needle point cap, when urged, causes the needle point cap 110 to rotate about the needle point to prevent the needle point from passing through the hole 114.

FIGS. 1 & 2 show the enclosing member or top wall or lid 118 that is rotated about the needle point cap-to-enclosing member attachment so as to enclose the needle point cap 110. The enclosing member or enclosing means 118 has a bore or hole 122 to allow the needle to pass through. In this embodiment, the enclosing member or needle shaft engaging means 118 acts as a fulcrum which engages the needle. The fulcrum or needle shaft engaging means 118 engages the needle and provides a pivot point used for rotating the needle point cap when the needle is passing through enclosing member hole 122 but not through bottom wall hole 114.

In the embodiment shown in FIGS. 1 & 2, the needle point guard safety cap assembly 100 is adapted to be attached to the needle hub or syringe. The needle point cap 110 is coupled to the collapsible extension or collapsible member or collapsible segmented extension 130 which in turn is coupled to the syringe attachment member or base cup 150. The syringe attachment member 150 is used to connect the needle point guard assembly to the needle hub or syringe. In the presently preferred embodiment, the needle point cap 110 to collapsible member 130 coupling means is by direct coupling.

The base cup 150 has a circumferential wall 152 and a bottom wall 154. The bottom wall 154 has the hole 156 to allow the needle to pass through. In this particular embodiment, slats 158, which define channels in the inside of the circumferential wall 152 near the bottom wall 154, are included to allow for easy attachment of the base cup 150 to the needle hub. Also included in this embodiment are attachment arms 160 extending from the base cup 150 near the bottom wall 154. The attachment arms 160 are used to couple the base cup 150 to the collapsible member 130. The attachment arms 160 are flexibly connected to the collapsible member 130.

The base cup 150 of the preferred embodiment has an annular slot 186 to engage a corresponding annular ring 206 on the needle hub. The ring and slot are tapered in cross-section, making them easy to engage but difficult to separate. The preferred embodiment further includes a longitudinal slot 188 which engages a corresponding longitudinal slot 208 on the needle hub to allow the needle shield to be fixedly rotationally alligned with the cannula opening 220 of the needle.

In the presently preferred embodiment the collapsible member or extensible frame 130 has many uses. It is used for connecting the syringe attachment member.150 to needle point cover 110 and for releasably securing the needle point cap 110 distal from the needle point. It is also used for sliding the needle point cover 110 down the needle shaft and facilitates rotation of the needle point cap 110 about the needle point. Additionally, it assists in maintaining the rotated position of the needle point cover 110.

The collapsible segmented extension 130, as shown in FIGS. 1 & 2, can be comprised of a wishbone segment 132 and a lower segment 140. The wishbone segment 132 has two arms 134 and a base 136. The wishbone arms 134 are flexibly connected to the base cup attachment arms 160. The lower segment 140 has an upper end 142 and a lower end 144. The wishbone segment base 136 is flexibly connected to the upper end 142 of the lower segment 140. A lower end 144 of the lower segment is flexibly connected to the needle point cap 110. Mounted to the lower segment 140 are two clips 148.

The wishbone segment 132 forms an opening or means through which the clips 148 can extend when the collapsible segment 130 is folded. It also provides a means for allowing the protrusion 192 on the attachment member to engage the slot 194 when the collapsible segment 130 is folded, as described more fully below. This is more clearly shown in FIG. 6.

FIG. 2 shows a pressure platform 146 that ultimately contacts the lever arm 120 and causes rotation of the needle point cap 110. Rotation of the needle point cap 110 about the needle point is best shown in FIGS. 8 & 9 and will be more thoroughly discussed later.

FIG. 2 also shows a pair of protruding clips 148 that extend from the lower segment 140 to provide a protective position locking means. The clips 148 provide a means to secure the collapsible segmented extension 130 to the needle shaft after needle use. Securing the collapsible segmented extension 130 to the needle shaft ensures that the needle point cap 110 maintains its rotated or skewed position and also maintains the protective position of the needle point cap 110 so that it can not slide back up the needle shaft and expose the needle point.

FIG. 9 shows one of the clips 148 engaging the needle shaft and securing the collapsible segmented extension 130 to the needle shaft. FIG. 10 is a cross-section through the clip, indicating how they engage the needle shaft.

FIG. 3 shows how base cup 150 is rotated in preparation for needle passage through the base cup 150 and attachment to the syringe. The Slats 158 provide a means to orient and prevent rotation of the needle within the base cup when a syringe is attached to or separated from a needle seated in the base cup. The base cup or syringe attachment member 150 also has a protrusion 192 with an enlarged head. The protrusion releasably engages the slot 194 in the lower segment 140 to provide a locking means when the collapsible extension 130 is collapsed as shown in FIGS. 6 & 7.

FIG. 3 also shows how the enclosing member 118 is rotated to enclose the needle point cap 110 to form a chamber 128 shown in FIG. 4. In the presently preferred embodiment, the hole or bore 122 in the enclosing member 118 has partially beveled edges 124. The partially beveled edges 124 allow the needle point cap 110 to more easily rotate about the needle point as is evident in FIG. 9.

In the preferred embodiment shown in FIG. 3, the needle point cap 110 has a well chamber 126 located adjacent to the hole or bore 114. It helps prevent the accidental re-emergence of the needle point through the hole 114 by capturing the needle point after the needle point cap 110 has been rotated about the needle point.

FIG. 4 depicts the base cup 150 after rotation and shows the direction of needle insertion in preparation for attachment of the needle point guard safety cap assembly 100 to the syringe. FIG. 4 also depicts the enclosed point cap 110 having the chamber 128. In this presently preferred embodiment, the chamber not only covers the point of the needle but also serves to capture fluid that might exude from the needle point.

The arrow adjacent the enclosed needle point cap 110 in FIG. 4 indicates the direction the enclosed needle point cap 110 is rotated in preparation for attachment of the needle point guard safety cap assembly 100 to the syringe. Rotation of the base cup 150 and the enclosed needle point cap 110 allows the needle to pass through both of them in preparation for attachment of the needle point guard safety cap assembly 100 to the syringe.

FIG. 5 depicts the needle point guard safety cap assembly 100 attached to the syringe 190 in preparation for receiving a needle sheath 300. Although in the presently preferred embodiment it is attached to the needle hub 204, it is also possible to attach it to syringe barrel 202.

As shown in FIG. 5, the collapsible extension 130 is beginning to collapse as the needle point guard safety cap assembly is installed in preparation for application of needle sheath 300. FIG. 5 also shows how one of the clips 148 will ultimately extend between the arms 134 of the wishbone segment 132 when the collapsible extension 130 is collapsed.

FIG. 6 shows the extension 130 collapsed or folded with one of the clips 148 extending between the arms 134 of the wishbone segment 132. Both of the clips 148, as is evident from FIG. 6 will extend between the arms 134 of the wishbone segment 132 when the collapsible extension 130 is folded.

FIG. 5 also depicts the base cup 150 protrusion 192 and the slot 194 in the collapsible extension prior to needle sheath 300 application. The arms of the wishbone segment 13? allow the protrusion 192 to engage the slot 194.

As is evident from FIG. 6 the needle point cap 110 is adapted to receive the needle sheath 300 to protect the needle from contaminants prior to use. In the presently preferred embodiment, the enclosing member or top wall 118 abuts the bottom wall 154 of the base cup 150 to prevent needle contamination. The syringe with the needle point guard safety cap assembly 100 and the needle sheath 300 installed as depicted in FIG. 6, is as the user would receive it prior to use. To use the syringe, the user simply removes the needle sheath and proceeds to use the syringe in the normal manner depicted by FIG. 7. The protrusion 192 on the attachment member and slot 194 in the collapsible extension keep the needle point cap 110 from sliding down the needle shaft while the needle sheath 300 is being removed.

Subsequent to use, the user simply urges the folded collapsible extension 130 with his finger to dislodge the enlarged head of protrusion 192 from the slot 194. The passage of the enlarged head of the protrusion through the slot provides tactile feedback to the user that the needle shield has actuated; also, in applying sufficient pressure to force the head through the slot, it is assured that the user's finger has sufficient momentum to fully actuate the needle shield.

The user then continues to urge the collapsible extension 130 to cause the needle point cap 110 to slide the length of the needle as shown in FIG. 8. In the presently preferred embodiment, as the needle point cap 110 nears the needle point, the pressure platform 146 nears and ultimately contacts the lever arm 120. After contact, further urging of the collapsible extension 130 causes a force to be applied to the lever arm 120. Approximately coincident with contact, the needle point clears the hole 114 and becomes located within the chamber 128. After the needle point has cleared the hole 114 the needle point cap 110 rotates about hole 122, and hence about the needle point in response to urging of the lever arm 120. FIG. 9 shows the rotated needle point cap 110.

As collapsible extension 130 approaches the needle shaft in response to the urging of the user, the clips 148 engage or surround the needle so that the collapsible extension 130 is clipped in place as shown in FIG. 9. This provides a means to maintain or secure the rotated position of the needle point cap 110 with respect to the needle point by maintaining engagement of the pressure platform 146 with the lever arm 120 so as to prevent the needle point from re-emerging through the hole 114. It also serves provides a means to keep the collapsible extension 130 from folding and allowing the needle point cap 110 to slide back up the needle shaft thereby exposing the needle point. Therefore, the clips 148 provide a means for securing the needle point cover 110 in the needle-protective position. The clips also provide additional tactile feedback to the user as they engage the needle shaft.

In addition, in the presently preferred embodiment depicted in FIG. 9, the well chamber 126 serves to capture the needle point and prevent it from re-emerging through the hole 114. The well chamber also helps to capture fluid that might exude from the needle point so that it can not easily escape from the needle point cap. Furthermore, in preparation for disposal, needle sheath 300 can be placed over the needle point cap 110 for convenience and to ensure the capture of any excess fluid which might leak from the hole 114 in the bottom wall 116 of the needle point cap 110.

While only several embodiments of the invention have been described, numerous modifications or other embodiments could be made without deviating from the invention thus described in the following claims.

What is claimed is:

1. A needle point guard safety cap assembly for securely covering and protecting the needle point of a syringe after the syringe has been used, comprising:

a) a syringe attachment member operable to firmly attach the needle point guard safety cap assembly to the needle hub of a syringe;

b) a needle point cover member in the form of an elongated hollow member that is open at one end for receiving the needle therein, and at its other end is mostly enclosed by an end wall having a hole through which the needle can pass;

c) a lid adapted to close the otherwise open end of the cover member, the lid also having a hole through which the needle may pass so that the needle may extend through both holes;

d) an extensible frame having a proximal end and a distal end, the proximal end coupled to the syringe attachment member and the distal end coupled to the needle point cover; the extensible frame being manually actuable for advancing the cover member along the needle to where the end wall of the cover member is beyond the extremity of the needle point;

e) the needle point cover member then being supported by the hole in the lid and then, in response to further advancement of the cover member, rotating about the lid hole until the needle point passes inside the enclosed end wall of the cover member into a protected position where it cannot pass through the cover member hole.

2. A needle point guard safety cap assembly as in claim 1 wherein the lid is pivotally secured to the cover member; and the syringe attachment member, cover member, lid, and extensible frame are integrally formed of plastic material.

3. A needle point guard safety cap assembly as in claim 1, wherein the cover member further comprises a well chamber formed in the end wall adjacent to the hole for passage of the needle therein, the well chamber being operable for enclosing the sharp end of the needle once the needle point cover has be actuated, thereby preventing the sharp end of the needle from re-emerging through the hole.

4. A needle point guard safety cap assembly as in claim 3 further comprising a fulcrum on the needle point cover, with the extensible frame being further operable to act on the fulcrum when the end wall of the cover member is beyond the extremity of the needle point and thereby cause the cover member to rotate such that the sharp end of the needle enters the well chamber.

5. A needle point guard safety cap assembly as in claim 1, wherein the extensible frame further comprises a proximal frame segment and a distal frame segment, the frame segments coupled in the center of the extensible frame with a hinge, the hinge being in a closed position prior to actuation of the needle point cover with the proximal and distal frame segments lying substantially parallel to one another, with extension of the frame being acheived by opening the hinge.

6. A needle point guard safety cap assembly as in claim 5, further comprising at least one securing clip on the extensible frame, the securing clip being operable to irreversibly engage the needle when the needle point cover is fully actuated.

7. A needle point guard safety cap assembly as in claim 1, further comprising interlocking members on the syringe attachment member and the extensible frame, the interlocking members releasably securing the needle point guard safety cap assembly in its un-actuated state and providing a tactile indication when the needle point guard safety cap assembly is actuated.

8. A needle point guard safety cap assembly as in claim 7, wherein the interlocking member on the syringe attachment member comprises a protrusion having a bulbous enlarged end, and the interlocking member on the extensible frame comprises a slot of a width slightly less than the diameter of the bulbous end; the protrusion and slot being positioned on the syringe attachment member and extensible frame, respectively, such that when the needle point guard safety cap assembly is in its unactuated state with the needle point cover member most distal from the needle point the protrusion engages the slot with the bulbous end of the protrusion passing through the slot, whereby the needle shield is releasably maintained in its unactuated state.

9. A needle point guard safety cap assembly as in claim 1, wherein the syringe attachment member further comprises at least one annular slot to engage a corresponding annular ring on the needle hub of a syringe.

10. A needle point guard safety cap assembly as in claim 1, wherein the syringe attachment member further comprises at least one longitudinal slot to engage a corresponding longitudinal ridge on the needle hub of a syringe to maintain a fixed radial orientation of the needle point guard safety cap with respect to the cannula opening of the syringe.

11. A needle point guard safety cap assembly as in claim 1, wherein the needle point cover member is adapted to receive a needle sheath, thereby allowing the needle sheath to cover the needle when the needle point cover member is distal from the needle point.

12. In a needle point guard safety cap assembly having (1) a syringe attachment member operable to connect the needle point guard safety cap assembly to the needle hub of a syringe; (2) a needle point cover operable to enclose the needle tip when the needle point guard safety cap is actuated; and (3)an extensible frame having proximal and distal ends, the proximal end coupled to the syringe attachment member and the distal end coupled to the needle point cover,
    interlocking members on the syringe attachment member and extensible frame operable to releasably lock the needle point guard safety cap assembly in an unactuated state and to provide tactile feedback to the user when the needle point guard safety cap assembly actuation is initiated.

13. In a needle point guard safety cap assembly having (1) a syringe attachment member operable to connect the needle point guard safety cap assembly to the needle hub of a syringe; (2) a needle point cover operable to enclose the needle tip when the needle point guard safety cap is actuated; and (3)an extensible frame having proximal and distal ends, the proximal end coupled to the syringe attachment member and the distal end coupled to the needle point cover,
    at least one securing clip on the extensible frame to engage the needle shaft upon activation of the needle point guard safety cap assembly to prevent the needle tip from exiting the needle point cover and to provide tactile feedback to the user when the needle point guard safety cap assembly actuation is completed.

14. In a needle point guard safety cap assembly having (1) a syringe attachment member operable to connect the needle point guard safety cap assembly to the needle hub of a syringe; (2) a needle point cover operable to enclose the needle tip when the needle point guard safety cap is actuated; and (3)an extensible frame having proximal and distal ends, the proximal end coupled to the syringe attachment member and the distal end coupled to the needle point cover:
    (a) an inner chamber within the needle point cover operable to contain the needle tip when the needle point guard safety cap assembly is actuated, and a needle entry hole and needle exit hole in communication with the inner chamber, the syringe needle passing through the entry hole, inner chamber, and exit hole prior to actuation of the needle point cover, and then withdrawing from the exit hole upon actuation such that the needle tip is within the inner chamber;
    (b) a fulcrum integral with the needle point cover and which upon actuation of the needle point guard safety cap assembly contacts the shaft of the needle, the fulcrum operable to cause the needle point cover to rotate with respect to the needle shaft;
    (c) a lever arm also integral with the needle point cover, the lever arm operable to apply rotational force to the needle point cover; and
    (d) a pressure platform integral with the extensible frame, the pressure platform operable to apply pressure to the lever arm when the needle point guard safety cap assembly is actuated and the syringe needle tip is within the inner chamber, causing the needle point cover to rotate such that needle tip cannot re-emerge from needle point cover through the exit hole.

15. A needle point guard safety cap assembly for securely covering and protecting the needle point of a syringe after the syringe has been used, comprising:
    a) means for firmly attaching the needle point guard safety cap assembly to the needle hub of a syringe;
    b) a needle point cover in the form of an elongated hollow member that is open at one end for receiving the needle therein, and at its other end is mostly enclosed by an end wall having a hole through which the needle can pass;
    c) means for enclosing the otherwise open end of the cover member, but permitting a needle to pass through;

d) frame means coupled to the syringe attachment means and the distal the needle point cover means; the frame means being manually actuable for advancing the cover member along the needle to where the end wall of the cover member is beyond the extremity of the needle point;

e) the cover member then being supported by the hole in the lid and, as it advances, rotating about the lid hole until the needle point passes inside the enclosed end wall of the cover member into a protected position where it cannot pass through the cover member hole;

f) the needle point guard safety cap assembly being integrally formed.

16. A needle point guard safety cap assembly as in claim 15 further comprising manually actuated locking means for securing the cover member in the needle-protective position.

17. A needle point guard safety cap assembly as in claim 15 further comprising a means for releasably locking the cover in a position distal from the point.

18. A needle point guard safety cap assembly comprising:

a) a base cup comprising;
   (i) a circumferential wall with a bottom wall attached thereto for defining a cup,
   (ii) the cup being adapted to attach to a syringe,
   (iii) the bottom wall of the cup having a hole therethrough to allow passage of a needle,
   (iv) a pair of attachment arms extending outward from the circumferential wall near the base cup bottom wall, and
   (v) a locking protrusion extending from the circumferential wall near the base cup bottom wall;

b) a collapsible segmented extension having at least two segments comprising:
   (i) a wishbone segment having two arms and a base, the arms being flexibly attached to the base cup attachment arms such that the base cup can rotate about the axis formed by the attachment arms to wishbone connection; and
   (ii) a lower segment having upper and lower ends, the upper end being flexibly attached to the wishbone base, the lower segment having a locking slot near the lower end for releasably locking the lower segment to the base cup locking protrusion when the segmented extension is collapsed and the lower segment is in a position adjacent the base cup; and c) a needle point cap flexibly connected to lower end of the lower segment, the needle point cap comprising:
   (i) a circumferential wall, a top wall, and a bottom wall which define a chamber; and
   (ii) the top wall and the bottom wall of the needle point cap each containing a bore therethrough to allow passage of the needle.

19. In a needle point guard safety cap assembly having a syringe attachment member and an extensible frame coupled to the syringe attachment member, a needle point cover coupled to the extensible frame, the needle point cover having the form of an elongated hollow member having a first end and a second end;

a lid member coupled to the needle point cover and closing the first end, the lid member having a hole formed therein for receiving the needle;

the needle point cover second end being mostly enclosed by an end wall having a hole through which the needle can be extended for use, the end wall further having a well chamber to engage and retain the sharp end of the needle when the needle is retracted.

20. The needle point cover of claim 19, further comprising a fulcrum member which may be acted upon by the extensible frame of the needle point safety cap assembly when the end wall of the cover member is beyond the extremity of the needle point, thereby causing the cover member to rotate such that the sharp end of the needle enters the well.

21. The need point guard safety cap assembly of claim 12, further comprising at least one securing clip on the extensible frame to engage the needle shaft upon activation of the needle point guard safety cap assembly to prevent the needle tip from exiting the needle point cover, the interlocking members and securing clip further serving to provide tactile feedback to the user when the needle point guard safety cap assembly actuation is initiated and completed, respectively.

22. The need point guard safety cap assembly of claim 13, further comprising interlocking members on the syringe attachment member and extensible frame operable to releasably lock the needle point guard safety cap assembly in an unactuated state, the interlocking members and securing clip further serving to provide tactile feedback to the user when the needle point guard safety cap assembly actuation is initiated and completed, respectively.

* * * * *